(12) United States Patent
Tydlaska et al.

(10) Patent No.: US 9,986,902 B2
(45) Date of Patent: Jun. 5, 2018

(54) LARYNGOSCOPE, LARYNGOSCOPE ARM AND LARYNGOSCOPE SYSTEM

(71) Applicant: Dilon Technologies, Inc., Newport News, VA (US)

(72) Inventors: Jay Tydlaska, Fort Worth, TX (US); Amy Sheppard, Fort Worth, TX (US)

(73) Assignee: Dilon Technologies, Inc., Newport News, VA (US)

( * ) Notice: Subject to any disclaimer, the term of this patent is extended or adjusted under 35 U.S.C. 154(b) by 184 days.

(21) Appl. No.: 15/144,413

(22) Filed: May 2, 2016

(65) Prior Publication Data

US 2016/0242637 A1 Aug. 25, 2016

Related U.S. Application Data

(60) Continuation-in-part of application No. 13/374,985, filed on Jan. 27, 2012, now Pat. No. 9,351,633, which is a division of application No. 12/750,784, filed on Mar. 31, 2010, now Pat. No. 8,864,657.

(60) Provisional application No. 61/437,010, filed on Jan. 28, 2011, provisional application No. 61/165,091, filed on Mar. 31, 2009.

(51) Int. Cl.
| | |
|---|---|
| *A61B 1/267* | (2006.01) |
| *A61B 1/04* | (2006.01) |
| *A61B 1/00* | (2006.01) |
| *A61B 1/06* | (2006.01) |
| *A61B 1/05* | (2006.01) |
| *A61M 16/04* | (2006.01) |

(52) U.S. Cl.
CPC .......... *A61B 1/267* (2013.01); *A61B 1/00052* (2013.01); *A61B 1/00066* (2013.01); *A61B 1/00101* (2013.01); *A61B 1/00105* (2013.01); *A61B 1/05* (2013.01); *A61B 1/00016* (2013.01); *A61M 16/0488* (2013.01); *A61M 2205/3569* (2013.01); *A61M 2205/3592* (2013.01); *A61M 2205/502* (2013.01); *A61M 2209/082* (2013.01)

(58) Field of Classification Search
CPC . A61B 1/267; A61B 1/00052; A61B 1/00066; A61B 1/00105; A61B 1/053
See application file for complete search history.

(56) References Cited

U.S. PATENT DOCUMENTS

| | | | | |
|---|---|---|---|---|
| 2,354,471 A | * | 7/1944 | MacIntosh | A61B 1/267 600/199 |
| 2,646,036 A | * | 7/1953 | Allyn | A61B 1/267 403/27 |
| 4,579,108 A | * | 4/1986 | Bauman | A61B 1/267 600/186 |
| 4,832,020 A | * | 5/1989 | Augustine | A61M 16/0488 128/207.14 |

(Continued)

*Primary Examiner* — Christian Sevilla
(74) *Attorney, Agent, or Firm* — Decker, Jones P.C.; Brian K. Yost; Geoffrey A. Mantooth

(57) ABSTRACT

A laryngoscope and system are provided, the laryngoscope comprising a handle, an arm, a camera harness comprising a deployable camera, and a light. The arm comprises a first canal adapted to receive the camera upon deployment and a second canal adapted to transmit light from the handle into an oral cavity. The handle comprises a remote ejection element. The laryngoscope system comprises a handle capable of direct wireless communication with a display unit.

18 Claims, 19 Drawing Sheets

(56) References Cited

U.S. PATENT DOCUMENTS 5,487,607 A * 1/1996 Makita .................... A61B 5/01
374/121

* cited by examiner

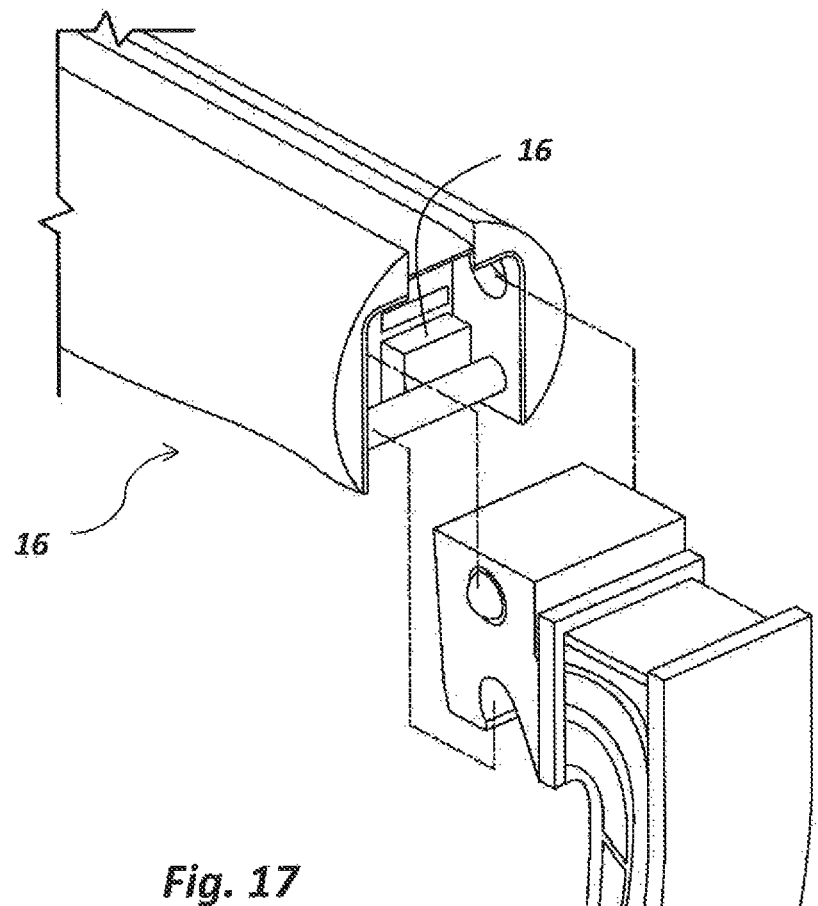
Fig. 17
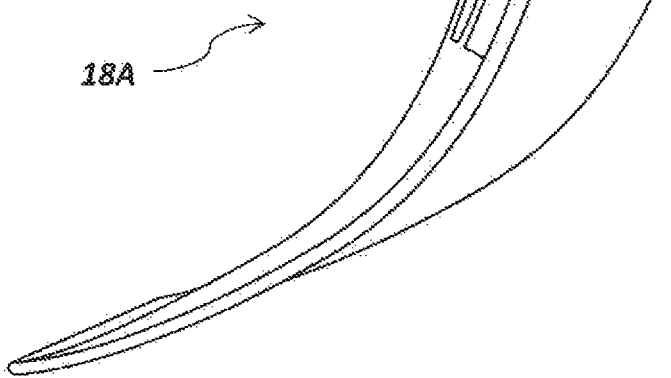

LARYNGOSCOPE, LARYNGOSCOPE ARM AND LARYNGOSCOPE SYSTEM

This application is a Continuation-in-Part of application Ser. No. 13/374,985 ("'985 application") which claims priority from provisional application 61/437,010 filed Jan. 28, 2011, said '985 application being a Divisional Application of application Ser. No. 12/750,784, now U.S. Pat. No. 8,864,657, which claims the benefit of provisional application Ser. No. 61/165,091 filed Mar. 31, 2009, the contents of which are incorporated by reference herein their entirety.

BACKGROUND OF THE INVENTION

1. Field of the Invention

The present invention relates generally to an airway management device and system and specifically to a laryngoscope, a laryngoscope arm, and a laryngoscope system capable of allowing a health care provider to establish an airway.

2. Description of the Prior Art

Over 20 million intubation procedures are performed each year in the United States either as a routine part of surgery or in emergency situations resulting from trauma, cardiopulmonary arrest or other disease processes. In an intubation procedure, it is necessary to insert an endotracheal tube (ET tube) in order to maintain a patients respiratory function. The tube is inserted into a patients trachea via either the mouth or nasal tract so that the airway remains open and oxygen reaches the patient's lungs.

Practitioners use an instrument known as a laryngoscope to help in the placement of the ET tube. This instrument typically comprises a handle, a blade, and a light. The practitioner uses the device to move the tongue and epiglottis to one side so that the airway may be properly identified. Once the airway is properly identified, the practitioner inserts the tube with one hand while holding the laryngoscope with the other. In a small percentage of patients, the airway cannot be identified with the laryngoscope alone. With these patients, practitioners sometimes use a device known as a "bougie". This bougie is a small diameter flexible cylinder of metal, plastic or other material that may serve as a guide for placement of a larger ET tube.

The laryngoscope predominantly used today to accomplish this task was developed in the 1940's. When performed by an experienced practitioner, the procedure is usually quick and uneventful. However, even in the hands of well skilled individuals, there is still an unacceptable number of occurrences in which placement of the endotracheal tube is difficult or impossible resulting in an inability to provide the patient with oxygen leading to death or injury. Difficulty in placing the endotracheal tube may be due to trauma, abnormal anatomy, disease processes or for unknown and unpredictable reasons.

Over the years, there have been many attempts to improve upon the design of the original laryngoscope but those attempts have been largely unsuccessful as evidenced by the continued use today of virtually the same device developed in the 1940's. More recently due to advances in miniaturization of technology, devices have been developed known as video laryngoscopes that greatly improve the ability to adequately locate the vocal cords and appropriately place the endotracheal tube. These devices are generally constructed with a small camera placed at the distal end of the laryngoscope and the image obtained by that camera is viewed on a remote monitor. However, these devices are expensive and often inconvenient to use. Moreover, prior art devices still fail to offer a solution to the difficult intubations in which a bougie is necessary.

What is needed is an inexpensive, sanitary, easy to use laryngoscope system that may be used in all situations, including the most difficult intubations in the most challenging environments.

SUMMARY OF THE INVENTION

It is an object of the invention to provide an inexpensive, sanitary, easy to use laryngoscope system that may be used in all situations, including most difficult intubations in the most challenging environments.

The present invention generally provides a laryngoscope capable of being connected to a monitor and power source, said laryngoscope being comprised of a handle, an arm, a camera, a light, and a disposable sheath; wherein the sheath is slideably and removably coupled to the arm; the sheath being further comprised of a canal capable of being threaded with a bougie; the handle being further comprised of a remote ejection element mechanically connected to a spring element capable of ejecting the sheath from the arm; the arm being removably coupled to the handle. The system is further comprised of a display device, and an IV pole attachment. The sheath may be remotely ejected by depressing a thumb ejector switch on the handle which releases a clasp at the coupling point and further releases a spring element held in compression which, upon release, forcibly moves the sheath along the length of the arm, such that the sheath becomes detached from the arm. The sheath is further comprised of a small canal at least partially running along the outside length that serves as a guide for the bougie. With the laryngoscope properly placed, the practitioner may thread a bougie through the sheath's bougie canal into the airway and use this bougie as a guide for the ET tube.

The laryngoscope is further comprised of a light and a camera. The lens of this camera is located at the distal end of the arm and the signal is transmitted either wirelessly or through a cord to the display device. The light is also located at the distal end of the arm. The cord further transmits power from a power source to the light and camera. In one embodiment of the present invention, the camera is located in the arm of the camera with the lens positioned near the body of the camera. In another embodiment, the body of the camera is located in the handle and communicates with the lens through a cable. In still another embodiment of the present invention, the image collected by the lens is reflected on a mirror or prism.

The display unit is comprised of a container, a screen, and a battery. The container is configured such that it may be removably coupled to an IV pole attachment or sit upright when not attached to the IV pole attachment.

The IV pole is conventional and commercially available. The IV pole attachment is comprised of an attachment receiver that allows the user to quickly attach and separate the display unit from the IV Pole attachment an IV clamp with a "C" shaped opening, and a laryngoscope storage receptacle.

In one aspect of the present invention, the laryngoscope is comprised of a heating element.

In one aspect of the present invention, the laryngoscope is capable of being motion activated such that the laryngoscope is powered on upon movement.

In another aspect of the present invention, the laryngoscope is capable of being motion activated such that the laryngoscope is powered off when no movement is detected for a predetermined period of time.

In one aspect of the present invention, the screen is capable of being motion activated such that the screen is powered on upon movement.

In another aspect of the present invention, the screen is capable of being motion activated such that the screen is powered off when no movement is detected for a predetermined period of time.

In another aspect of the present invention, the arm is removably coupled to the handle.

In another aspect of the present invention, a user using the ejection element may eject the sheath without touching the sheath.

In another aspect of the present invention, the display unit is comprised of a stand such that said unit is capable of standing upright.

In another aspect of the present invention, the laryngoscope is capable of wirelessly communicating with the screen.

BRIEF DESCRIPTION OF THE DRAWINGS

FIG. 17 is an isometric view of the arm of FIG. 16 coupled to a handle of an alternative preferred embodiment.

DESCRIPTION OF THE PREFERRED EMBODIMENT

I. First Embodiments

Figure 1:
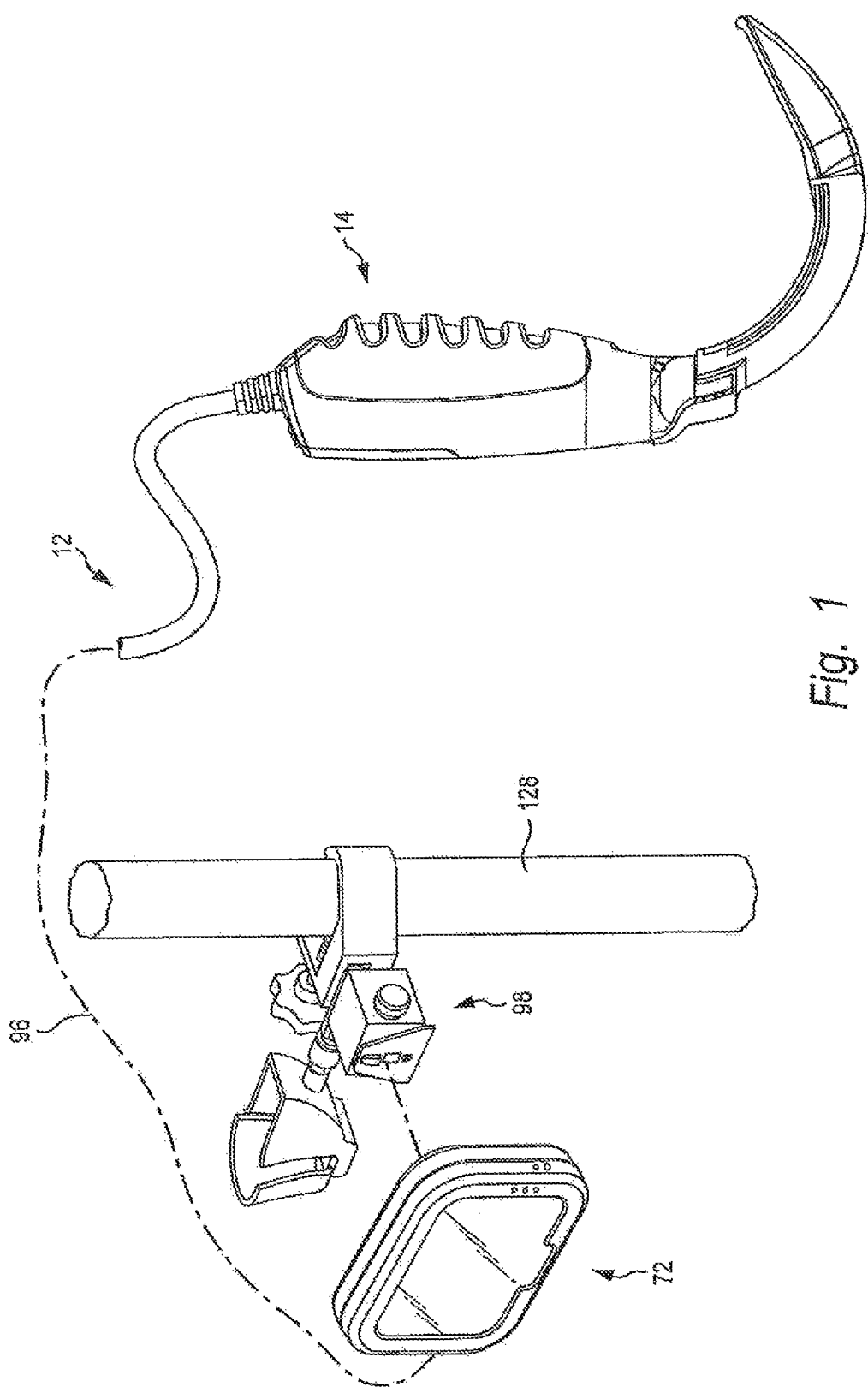
FIG. 1 is a side perspective view of the laryngoscope system in accordance with a preferred embodiment.

Referring to FIGS. 1-15 there is shown a laryngoscope system 12 of the present invention. This laryngoscope system 12 is generally comprised of a laryngoscope 14, a display unit 72, and an IV pole attachment 98 capable of being coupled to an IV pole 128.

Figure 2A:
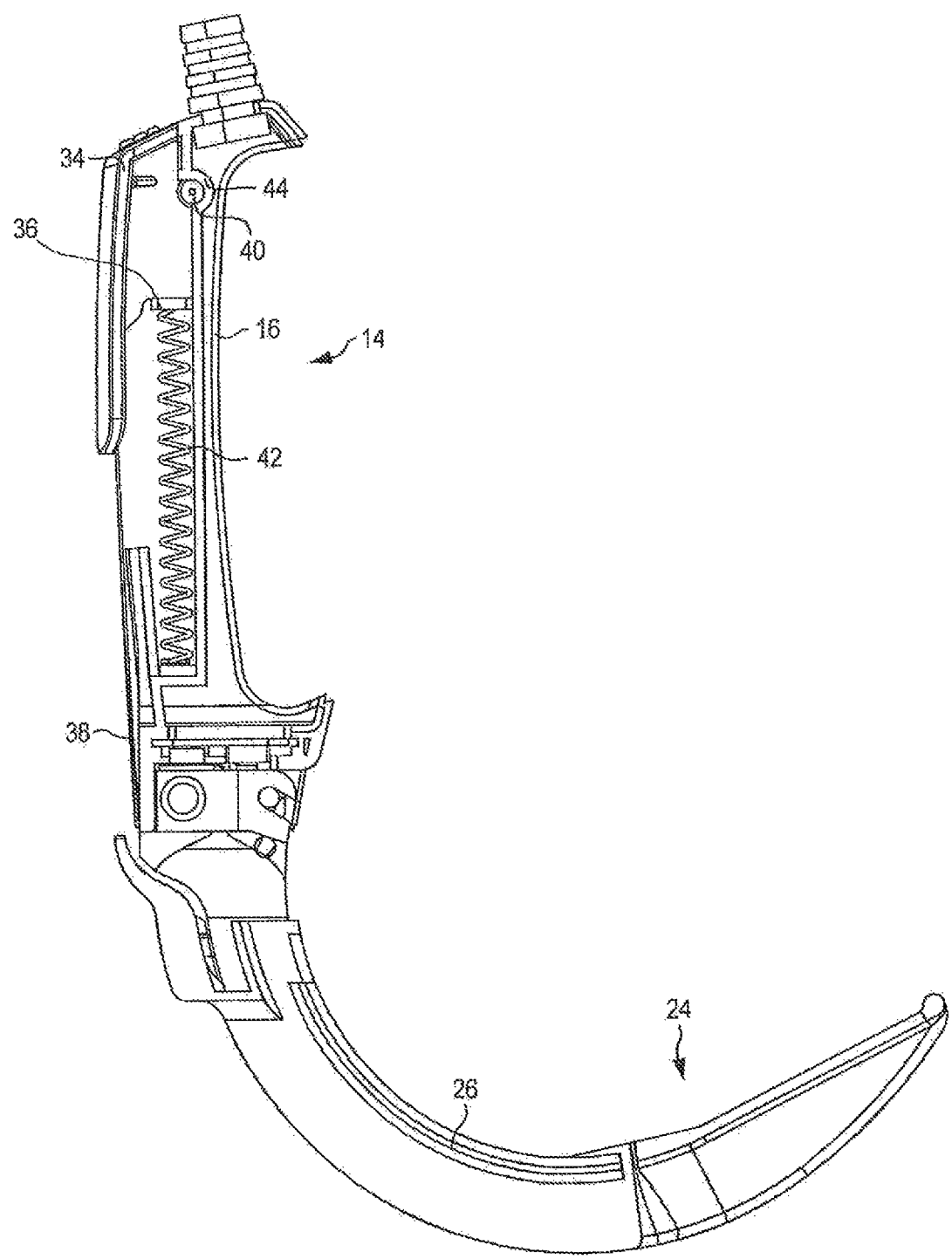
FIG. 2A is an isometric cut-away right side view of the laryngoscope in the open position with the arm and sheath attached in accordance with a preferred embodiment.
Figure 2B:
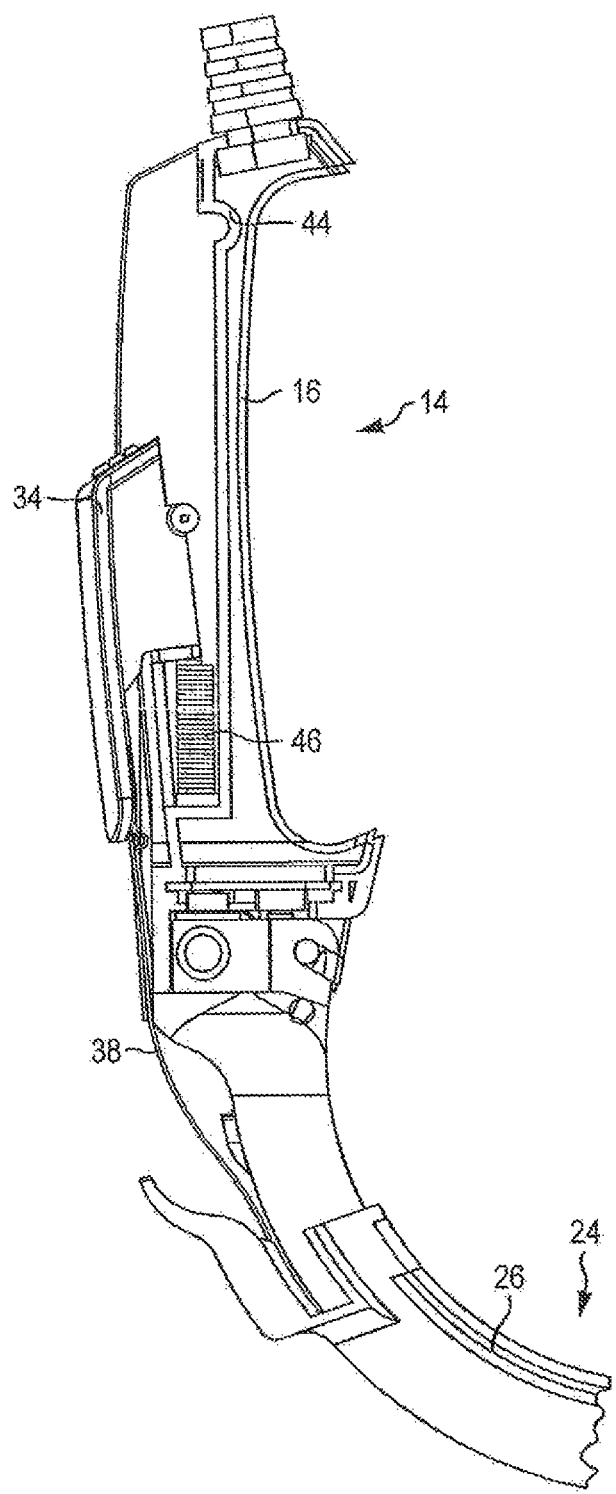
FIG. 2B is an isometric cut-away right side view of the laryngoscope of FIG. 2A with the thumb ejector switch in the extended position.
Figure 3:
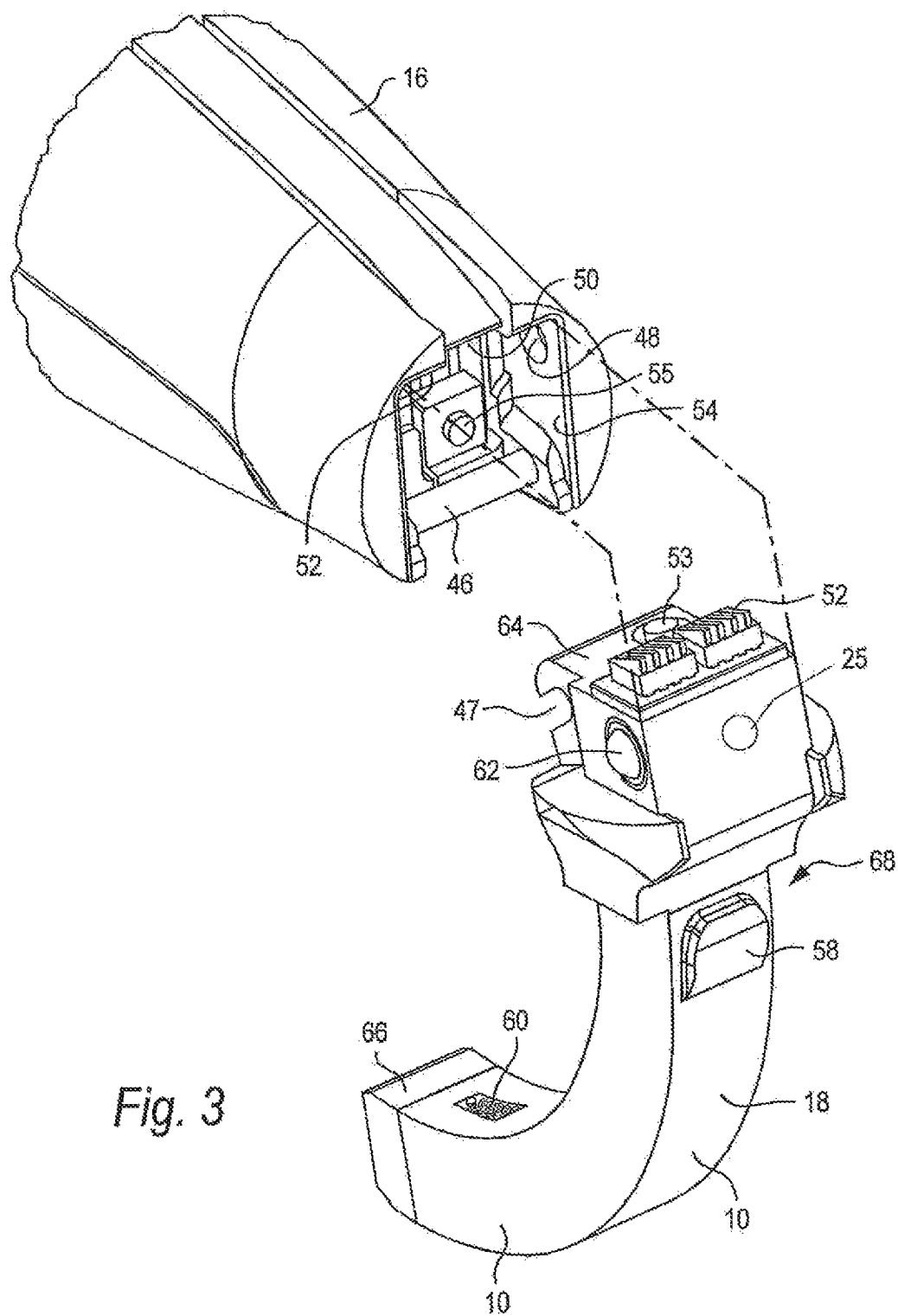
FIG. 3 is an isometric, rear, and side view of the laryngoscope arm and a partial view of the laryngoscope handle, in accordance with a preferred embodiment.
Figure 4:
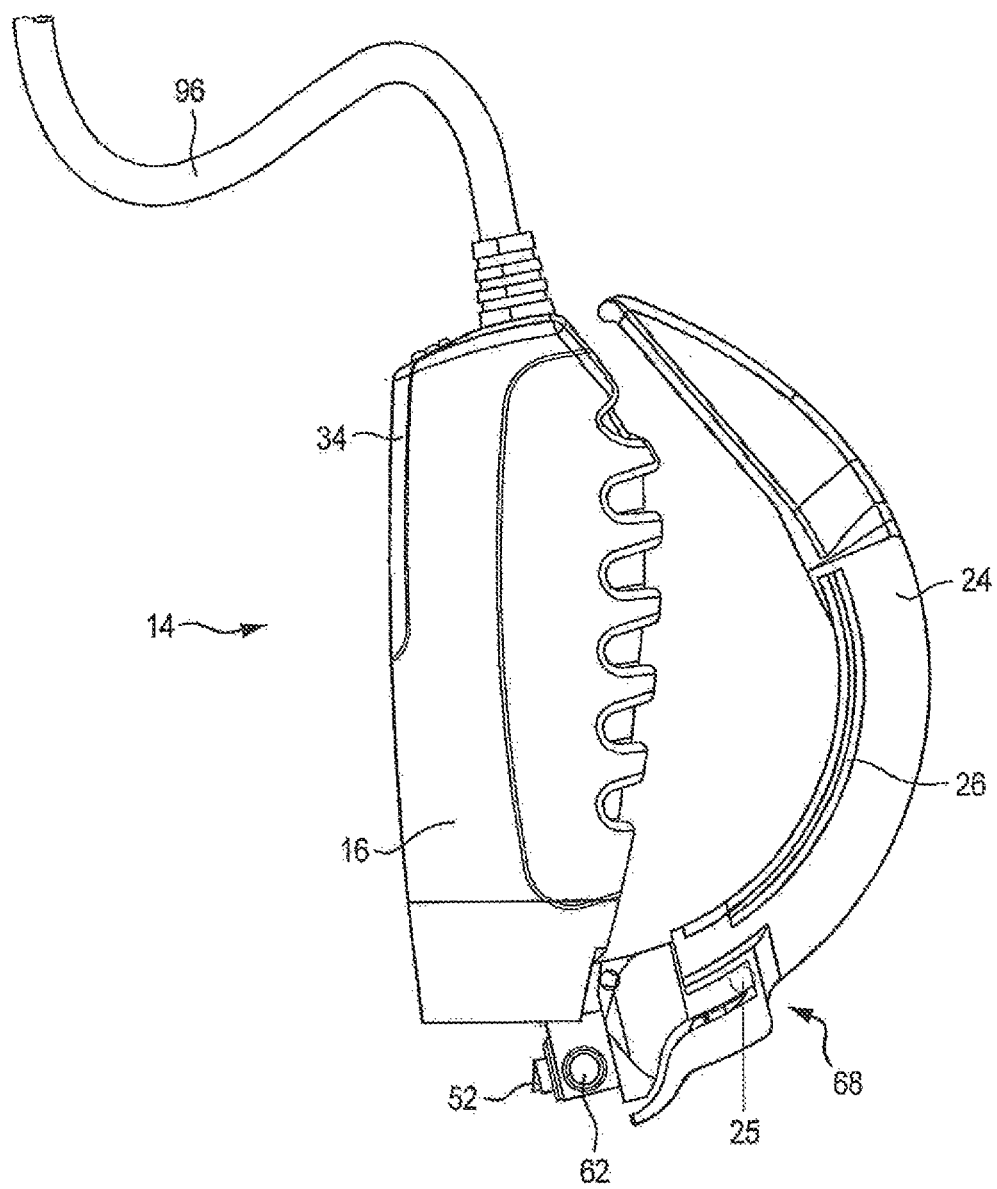
FIG. 4 is an isometric right side view of the laryngoscope with the arm in the closed position in accordance with a preferred embodiment.
Figure 5:
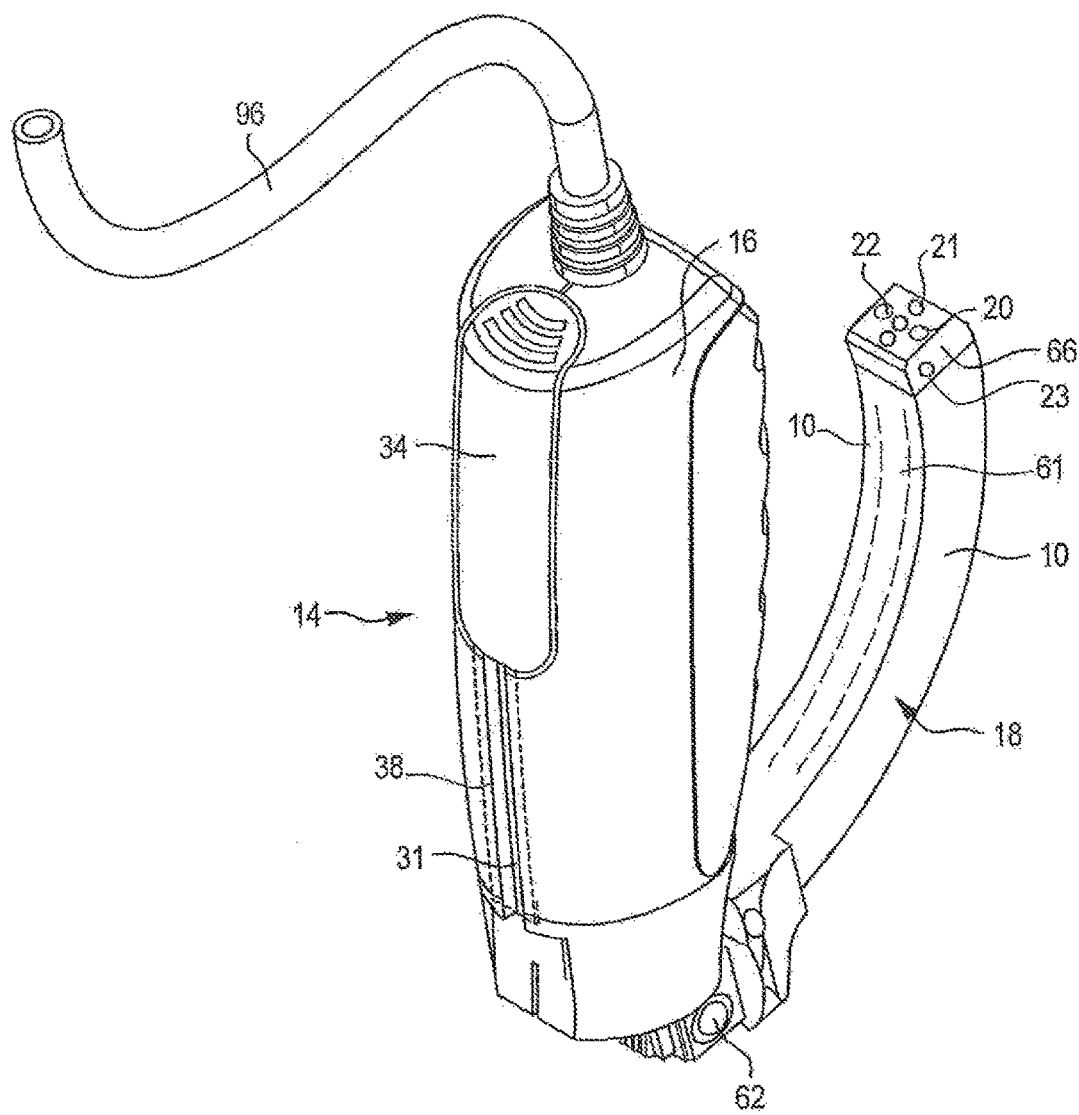
FIG. 5 is an isometric right side and rear view of the laryngoscope with the arm in the closed position without the sheath attached in accordance with a preferred embodiment.
Figure 6:
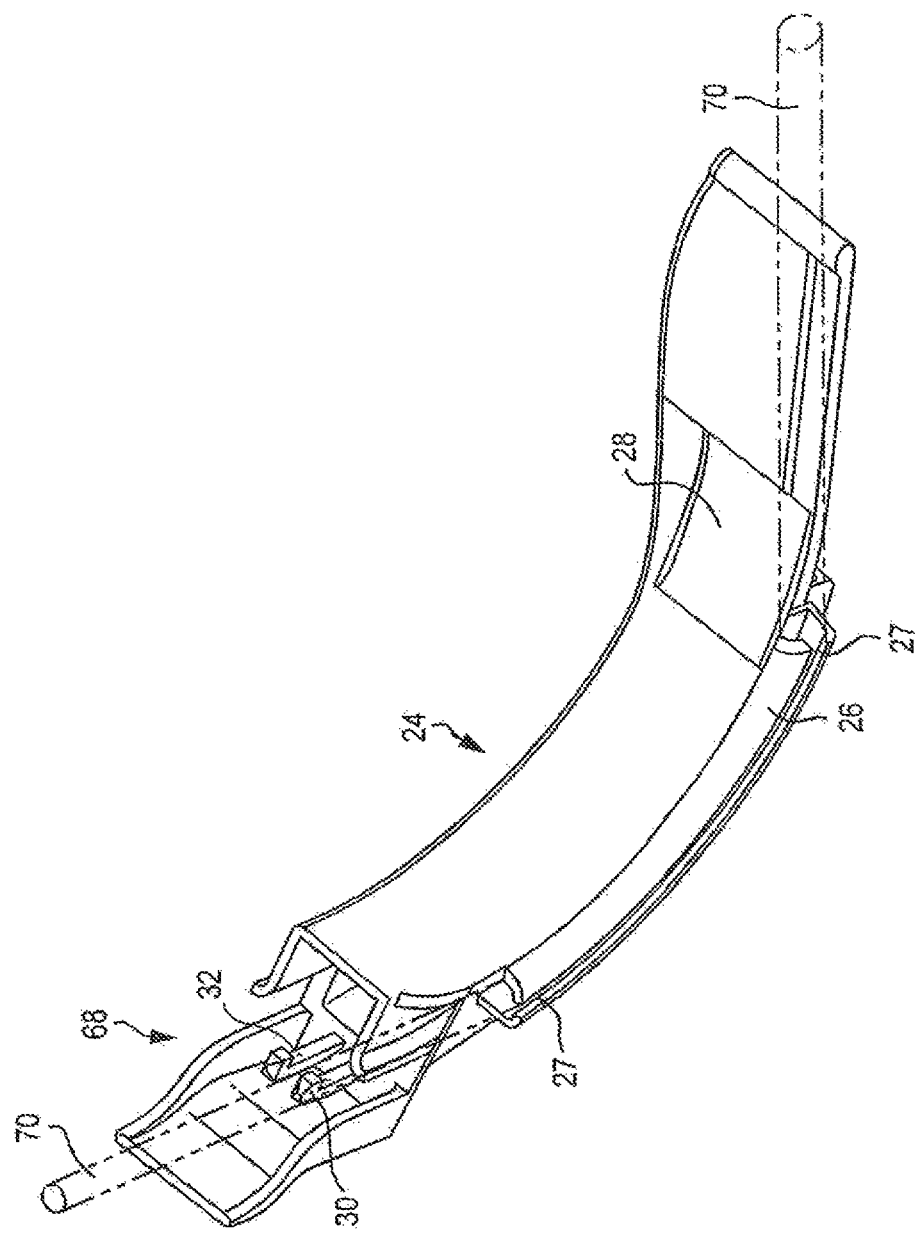
FIG. 6 is an isometric right side, top view of the sheath, in accordance with a preferred embodiment.

Referring to FIGS. 1-6, the laryngoscope 14 of the present invention comprises a handle 16, a curved blade or arm 18, a light 20, a camera 22, and a disposable sheath 24. The handle 16 of the laryngoscope 14 has a curved arm 18 attached. In one aspect of the present invention the arm 18 is removably coupled to the handle 16. Slideably coupled to the arm 18 is a sheath 24 which snaps into place at a coupling point 68 (FIG. 3). In the preferred embodiment, this sheath 24 is formed from plastic and is at least partially clear so as to allow light emitted from the light 20 to pass through it. Referring to FIG. 6, in the preferred embodiment, the sheath 24 is comprised of a transparent window 28. The sheath 24 has one or more clasps 30 on its proximal end (FIG. 6) which may be removably coupled to the arm 18 at the coupling point 68 (FIG. 3). In one aspect of the present invention, a user, using the thumb ejector switch 34, may eject the sheath 24 without physically touching the sheath 24. Referring to FIGS. 2A, 2B and FIG. 5, the thumb ejector switch 34 is located at the upper end of the handle 16. The thumb ejector switch 34 is comprised of a plunger block 36, an ejection rod 38, and a protrusion 40. The thumb ejector switch 34 is coupled to the ejection rod 38 which is coupled at the top end with the plunger block 36. The plunger block 36 is comprised of the protrusion 40. A return spring 42 is coupled to the thumb ejector switch 34. This return swing 42 maintains the ejection rod 38 in a retracted position as a rest state (FIG. 2A). Above the plunger block 36 is a retaining receptacle 44. This retaining receptacle 44 is structured and arranged such that it is capable of nesting the protrusion 40 and maintains the thumb ejector switch 34 in a rest position and prevents accidental deployment of the ejection rod 38.

Referring to FIGS. 2B, 3, 5 and 6, the sheath 24 may be remotely ejected by depressing the thumb ejector switch 34 (FIG. 2B) on the handle 16 which releases the clasp 30 at a sheath connection ridge 58 located on the arm 18 at the coupling point 68. The thumb injector switch 34, when depressed, travels down a switch channel 31 (FIG. 5). In one embodiment, thumb ejector switch 34 further releases a spring element 60 (FIG. 3) held in compression which, upon release, forcibly moves the sheath 24 along the length of the arm 18, such that the sheath 24 becomes detached from the arm 18. Referring to FIG. 6, in one aspect of a preferred embodiment, the clasp 30 has a score line 32 or thinner layer of material. This score line 32 creates a weakened area in the clasp 30 so that when depressed by the ejection rod 38, the clasp 30 is deformed at the score line 32. In one aspect of the present invention, the clasp 30, after ejection, cannot be returned to its original un-deformed configuration without breaking at the score line 32. Such breaking prevents the sheath 24 from being reused and thus, helps prevent contamination.

In one embodiment of the invention, and as shown in FIG. 6, the sheath 24 is further comprised of a small canal 26 running at least partially along the outside length that serves as a guide for a bougie 70. With the laryngoscope 14 properly placed, the practitioner may thread the bougie 70 through the sheath's bougie canal 26 into the airway and use this bougie 70 as a guide for an ET tube (not shown). As shown in the FIG. 6, in the preferred embodiment, this canal 26 is open on one side 27 such that the bougie 70 may be inserted and removed through this open side 27. This open side 27 permits the user to maintain the laryngoscope 14 in the airway while threading the ET tube over the bougie 70. In this embodiment, the bougie 70 is forced out of the canal 26 through the side opening 27 by the ET tube. In the preferred embodiment, this canal with its open side 27 is "C" shaped. This "C" shape helps maintain the bougie 70 within the canal 26 while still allowing the bougie 70 to be removed through the open side 27. Although the canal 26 of the preferred embodiment is open and forms a "C" shape, the canal 26 need not be open and need not be "C" shaped. Rather, the canal 26 can be closed on the sides so as to completely surround the bougie 70 along its length and can be circular or any other suitable shape.

As best shown in FIG. 5, the laryngoscope 14 also has a light 20 and a camera 22 positioned at the distal end of arm 18 and confined within arm walls 10 beneath a transparent cap 66. This cap 66 is clear and allows light to reach the lens 56 and light generated from the light 20 to exit the arm 18. A lens 56 for this camera 22 is located in the arm 18 and the signal is transmitted through a cord 96 to a display unit 72. While in the preferred embodiment the camera 22 is solid state and does not rely upon mirrors or prisms, the camera 22 may be comprised of a lens 56 that focuses light as an image on a prism. The image may then reflected by the prism to the camera 22.

Figure 12:
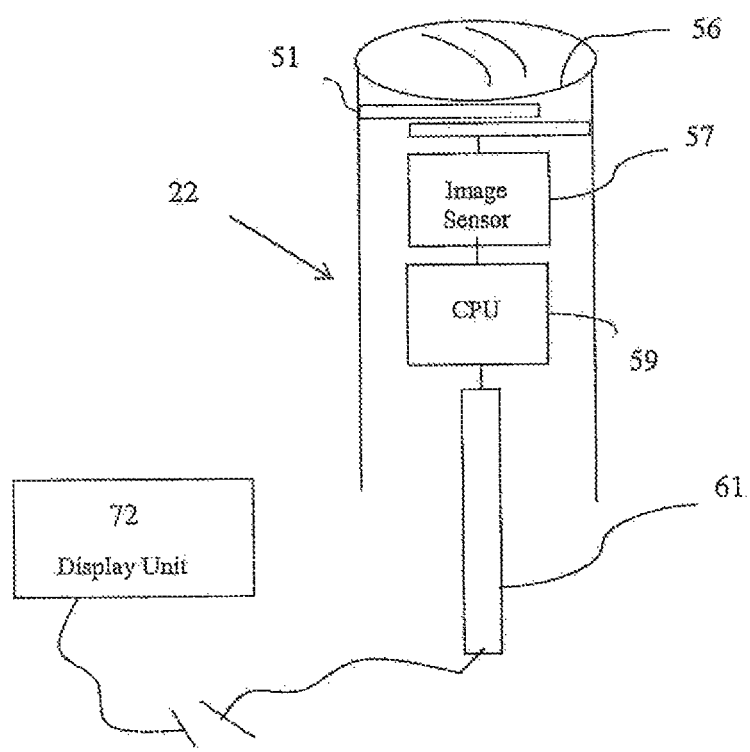
FIG. 12 is a block diagram depicting the camera unit.

Referring to FIGS. 5 & 12, the lens 56 of the camera 22 is also located at the distal end of the arm 18. In another embodiment, the main portion of the camera 22 is located in the handle 16 and communicates with the lens 56 through a fiber optic cable. In one embodiment, the camera 22 transmits the signal directly to the display unit 72 without the use of mirrors and prisms. In the preferred embodiment, the camera 22 is a complementary metal-oxide-semiconductor (CMOS) camera. However, other cameras 22 may be used including those incorporating charge-coupled device (CCD) technology.

In the preferred embodiment, the camera 22 transmits video images to the display unit 72. Referring to FIG. 12, the camera 22 is comprised of a lens 56, a shutter 51 an image sensor 57, a processor or CPU 59, and a flex circuit 61. Images collected by the camera 22 are displayed on the screen 88 of the display unit 72. Although the camera 22 of the preferred embodiment produces video images, it can also generate still images which may also be displayed on the screen 88 of the display unit 72.

Referring to FIG. 5, in the preferred embodiment, the arm 18 is comprised of a heating unit 21. This heating unit 21 heats the light 20 and camera 22 area and prevents the light 20 and camera 22 from developing moisture which may obscure the images gathered by the camera 22. The heating unit 21 is comprised of a thermistor 23 which monitors the temperature of the heating unit 21 and shuts the unit 21 off when a predetermined temperature is reached. In the preferred embodiment, such temperature is approximately 120 degrees Fahrenheit. The arm 18 is further comprised of a flex circuit 61 (FIG. 5). This circuit 61 is capable of supplying power to the camera 22 light 20 and heating unit 21 as well as transmitting information (including images) between the camera 22 and display unit 72. The handle 16 and arm 18 are each further comprised of heater switch 53 and 55. When the laryngoscope 14 is in the folded position, the heater switch 53 and 55 is in the open position and no power to the heater unit 21 is transferred. In this folded position, connectors 52 are also open such that power is not transferred to the light 20, camera 22, and heating unit 21.

As shown in FIGS. 3 & 4, in alternative embodiments, a sheath switch 25 is located on the arm 16. When the sheath 24 is in place and the arm 18 is in the working/engaged position as shown in FIGS. 2A and 2B, power is supplied to the heating unit 21. However, when the sheath 24 is not present, as shown in FIG. 3, or the arm 18 is in the folded/disengaged position depicted in FIG. 4, the heater switch 53, 55 is open, and no power is supplied to the heater unit 21. The sheath switch 25 interrupts power to the handle portion 53 of heater switch 53, 55.

Figure 13:
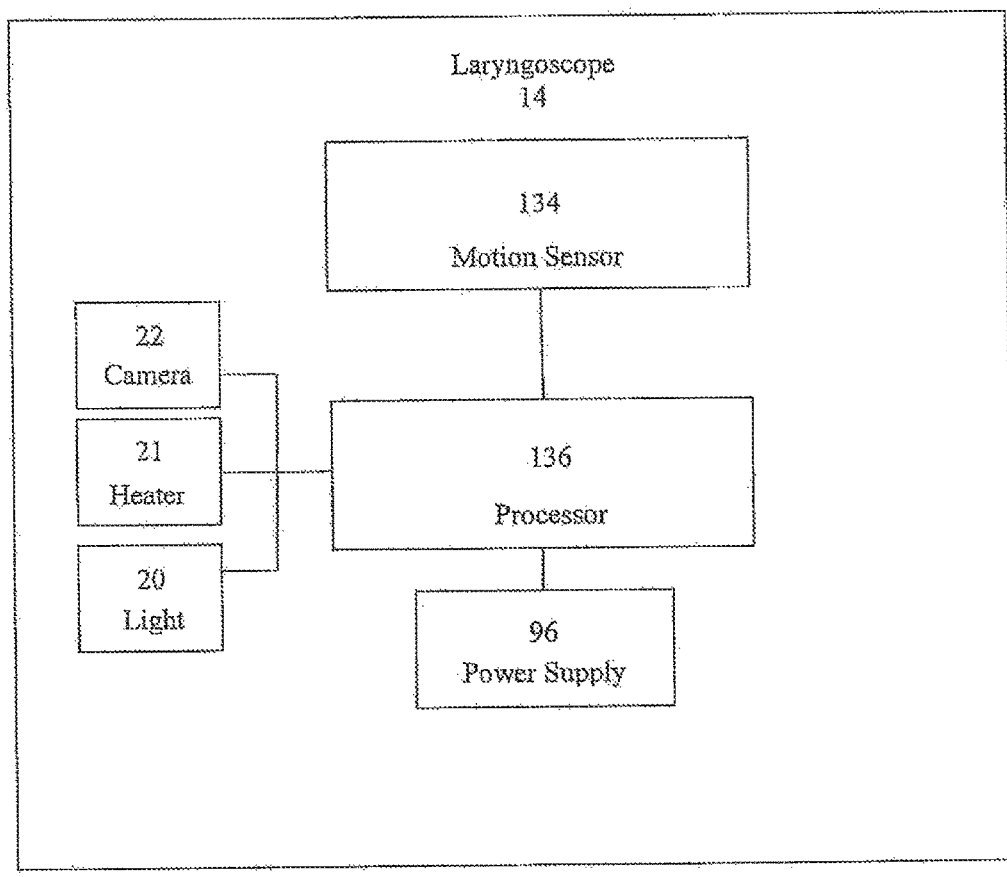
FIG. 13 is a block diagram depicting the laryngoscope motion sensor system.

The cord 96 further transmits power from a power source to the light 20 camera 22 and heating unit 21. Referring to FIG. 13, in one aspect of the present invention the laryngoscope 14 is comprised of a motion sensor 134 and processor 136 that allow the laryngoscope 14 to be motion activated such that the laryngoscope 14 is powered on upon a predetermined threshold of movement. In another aspect of the present invention, the laryngoscope 14 is capable of being motion activated such that the laryngoscope 14 is powered off when no movement is detected for a predetermined period of time.

In FIG. 3, there is shown the connection assembly between the handle 16 and arm 18. At the base of the handle 16 there is a pin 46 and ball spring receptacles 48. The arm 18 is comprised of ball springs 62. To couple the arm 18 to the handle 16, the pin 46 is inserted in arm opening 47. The ball springs 62 slide into ball spring receptacles 48. This connection aligns arm plate 64 with handle plate 50 within the walls 64 of handle plate 50 such that an electrical connection is made with connectors 52.

Figure 7:
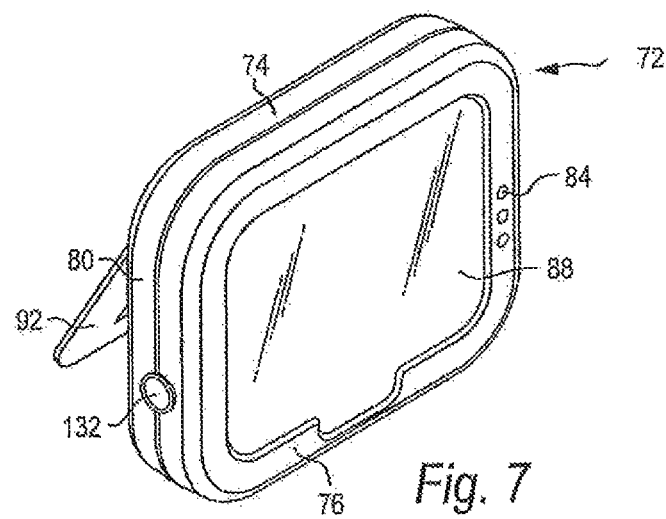
FIG. 7 is a top, front, and left side isometric view of the display unit with the stand in the open position.
Figure 8:
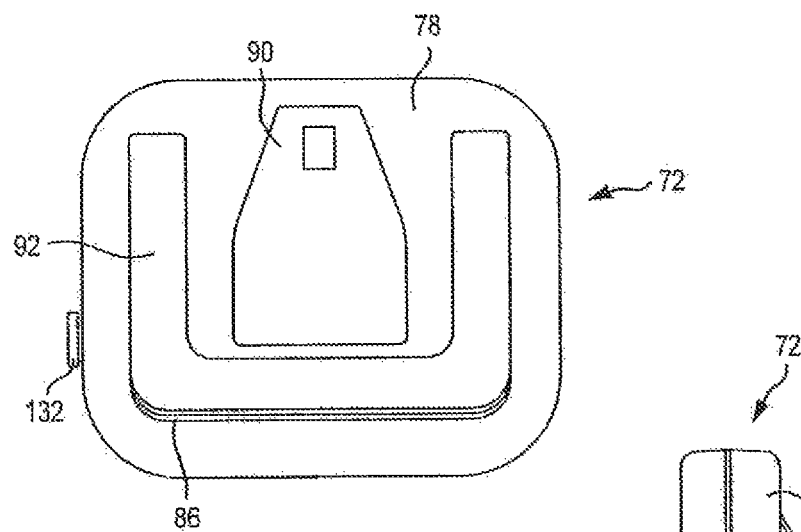
FIG. 8 is rear elevation view of the display unit with the stand in the open position.
Figure 9:
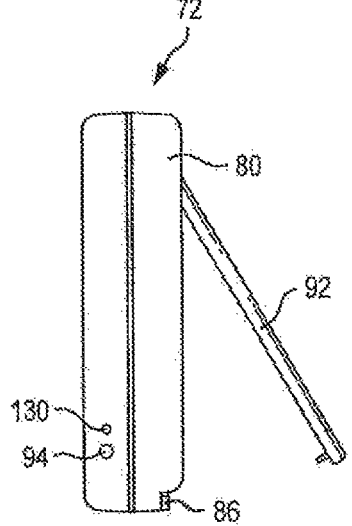
FIG. 9 is a right side isometric view of the display unit with the stand in the open position.

Referring to FIGS. 1 and 7-9, the display unit 72 is comprised of a thin container 74, a screen 88, a DC Jack 94, a battery management board and a battery. The container 74 is comprised of an IV pole attachment connector 90 such that it may be removably coupled to an IV pole attachment receiver 100 (FIG. 11) or, as shown in FIGS. 7 & 9, sit upright on a stand 92 when not attached to the IV pole attachment receiver 100. Referring to FIGS. 7-9, the container 74 of the preferred embodiment is generally rectangular and is comprised of a face 76, a back 78, and sides 80. The face 76 of the container 74 partially surrounds the screen 88 so that the screen 88 may be viewed. In the preferred embodiment, the stand 92 is pivotally coupled to the back 78 and is structured and arranged such that it extends generally rearward from the back 78 when in use and folds flat against the back 78 in a recess 86 when in the stored position. In the preferred embodiment, said recess 86 is contoured to the shape of the stand 92.

Figure 14:
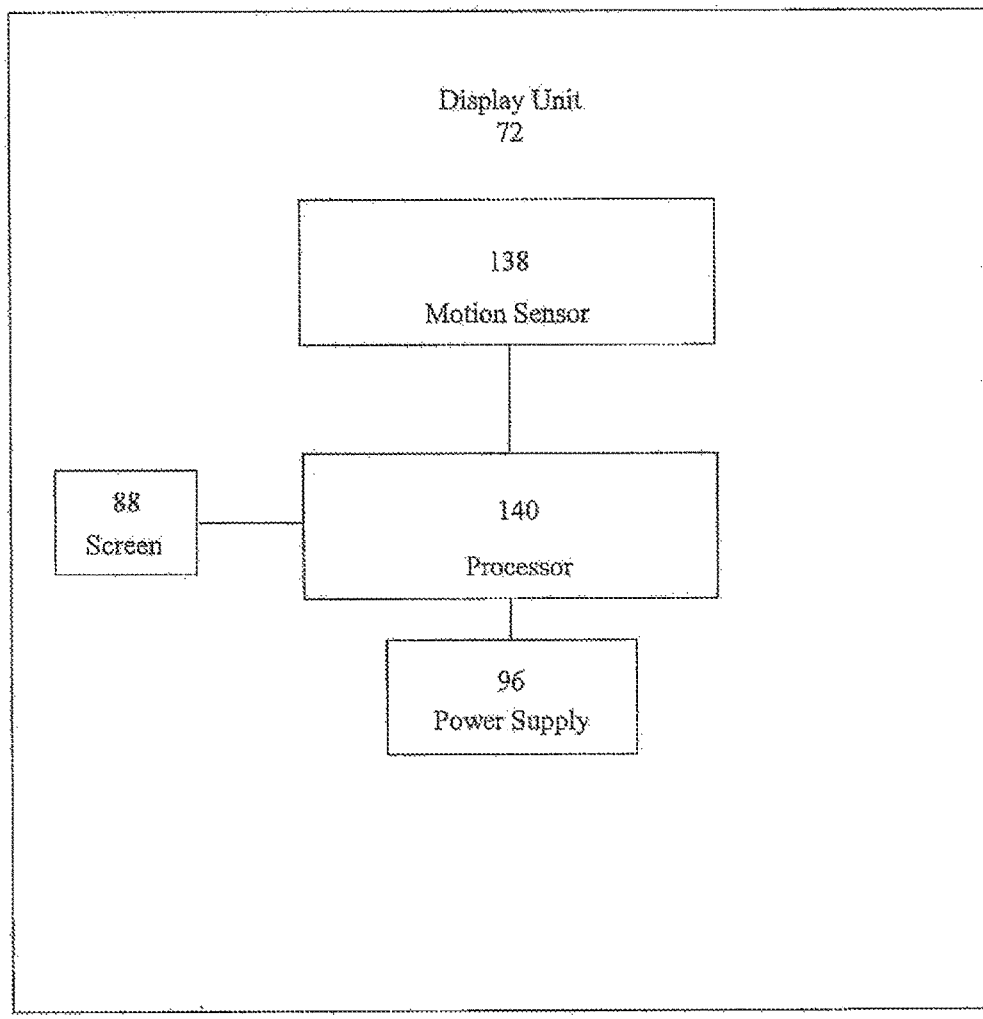
FIG. 14 is a block diagram depicting the display unit motion sensor system.

Referring to FIG. 14, in one aspect of the present invention the display unit 72 is comprised of a motion sensor 138 and processor 140 that allow the screen 88 to be motion activated such that the screen 88 is powered on upon a predetermined threshold movement. In another aspect of the present invention, the screen 88 is capable of being motion activated such that the screen 88 is powered off when no movement is detected for a predetermined period of time.

Referring again to FIGS. 7-9, in one aspect of the present invention, the face 76 has a battery status indicator 84. This indicator 84 is comprised of a plurality of LED lights. In the preferred embodiment, two green lights showing indicate to the user that the battery is fully charged and the system 12 is operable. An amber light indicates the battery is depleted and will need to be charged soon. A red light indicates the battery lacks sufficient charge to operate the screen 88, camera 22, and light 20. In the preferred embodiment, the indicator 84 is positioned at the lower portion of the face 76 near the center and beneath the screen 88.

The back 78, on the inside, has pegs and receptacles which act as coupling devices. The central pegs of the back correspond with receptacles located on the reverse side of the screen 88. The perimeter receptacles correspond with pegs located on the inside side of the face 76.

The screen 88 and battery are mounted on the inside portion of the back 78 of the container 74. The battery of the preferred embodiment is a rechargeable lithium battery and is capable of illuminating the screen 88. The screen 88 of the preferred embodiment is a 3.5 inch (Diagonal) Liquid Crystal Display (LCD). The screen 88 displays the image captured by the camera 22. In one aspect of the present invention, the screen 88 also displays other information such as the battery charge level, time, date, and the like.

The display unit 72 is further comprised of a DC input jack 94 and charge indicator 130. This jack 94 accepts the barrel portion of a charging cable. This jack 94 connects with and is used to recharge the battery The charge indicator 130 is an LED light that, when lit, alerts the user that the battery is being charged. In one aspect of the present invention, the unit 72 may not be operated while the charge cable is inserted into the jack 94

Figure 15:
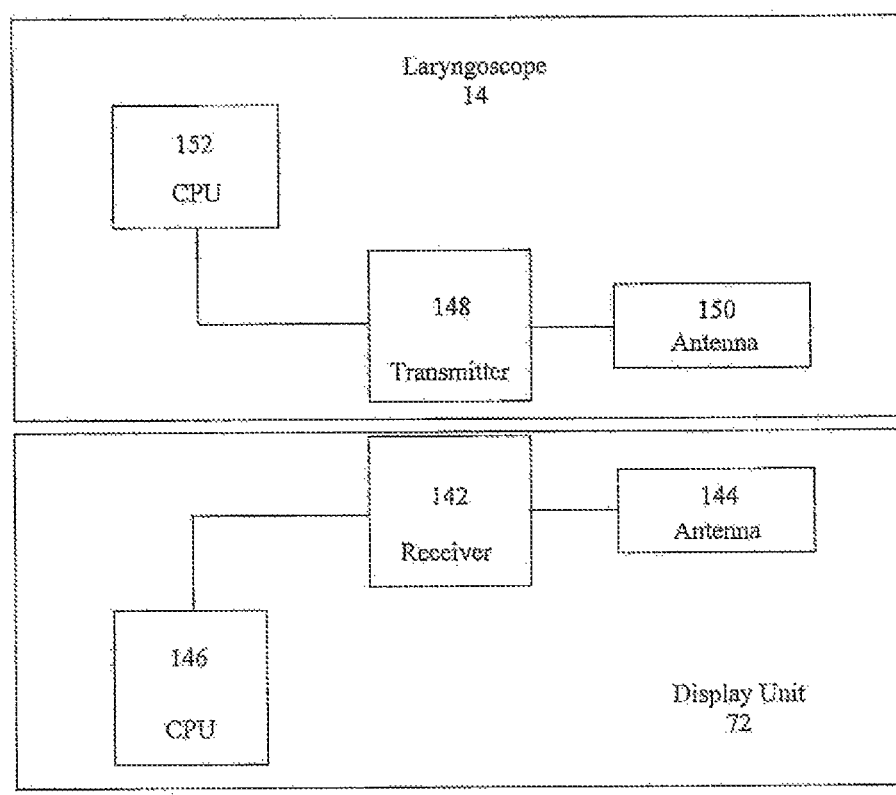
FIG. 15 is a block diagram depicting the laryngoscope and display unit wireless communication system.

The cable 62 is capable of communicating images received from the camera 22 to the screen 88 through the communication jack 132. Referring to FIG. 15, in one aspect of the present invention, the laryngoscope 14 is capable of wirelessly communicating with the display unit 72. In this embodiment, the laryngoscope 14 is further comprised of a transmitter 148, a processor or CPU 152 and an antenna 150. The display unit 72 is further comprised of a receiver 142, a processor or CPU 146 and an antenna 144. Images captured by the camera 22 are processed by the CPU 152 and transmitted wirelessly to the display unit 72 receiver 142 such that the images are displayed on screen 88.

The communication cable 6 is also capable of transmitting power generated by the battery to the light 20 and camera 22. The battery management board is a conventional and commercially available circuit board and is capable of maintaining an appropriate charge level in the battery.

The IV pole 128 is conventional and commercially available. As may be seen in FIGS. 1 and 10-11, the IV pole attachment 98 is comprised of an attachment receiver 100, an IV pole clamp 108 with a C shaped opening, a tightening screw 110 with wing knob 112, and a laryngoscope receptacle 114. The attachment receiver 100 allows the user to quickly attach and separate the display unit 72 from IV pole attachment 98 and is comprised of a bracket 102, and a quick release button 104. The attachment connector 90 of the display unit 72 may be slideably attached to the attachment receiver 100. The user may detach the display unit 72 from the attachment receiver 100 by depressing the release button 104 which activates a lever 106 that disengages the display unit 72 from the attachment receiver 100. The IV pole attachment 98 may be secured to an IV pole 128 by inserting the pole 128 in the IV clamp's 108 C shape opening and tightening the tightening screw 110 with the wing knob 112.

Figure 10:
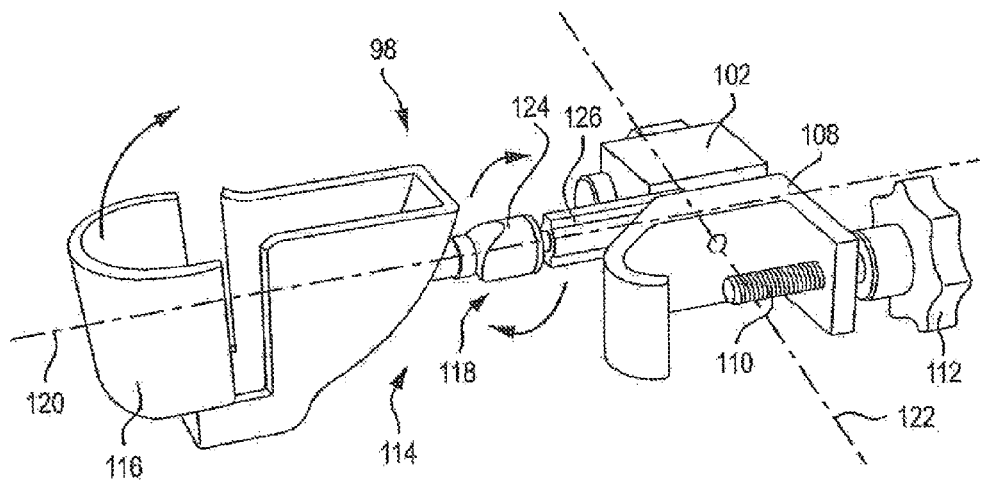
FIG. 10 is a rear isometric view of the IV pole attachment.
Figure 11:
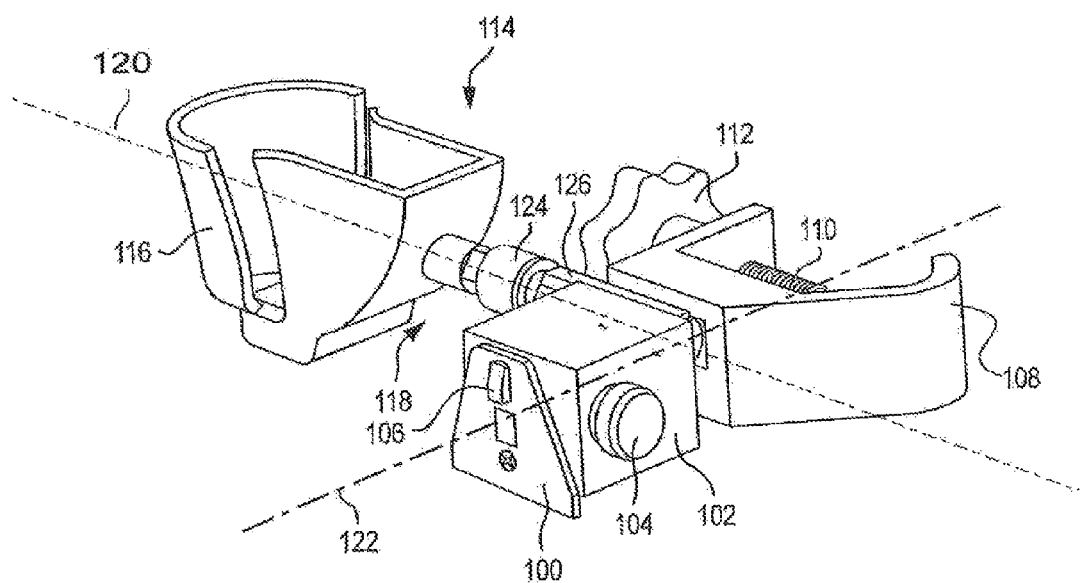
FIG. 11 is a front view of the IV pole attachment.

Referring to FIGS. 10-11, the laryngoscope receptacle 114 is comprised of a contoured holder 116 and an extension portion 118. The extension portion 118 is comprised of a first member 124 and a second member 126. In the preferred embodiment, the first member 124 is structured and arranged such that it can rotate 360 degrees around, an imaginary axis 120 that extends from a longitudinal axis of the extension portion 118. The second member 126 is structured and arranged such that it can rotate up to 360 degrees around an axis 122 perpendicular to the axis 120 around which the first member 124 rotates. Therefore, as may be seen in FIGS. 10 and 11, the receptacle 114, without the need for the user detaching the IV pole attachment 98 from the IV pole 128, can be positioned on either side of an IV pole 128 and oriented such that the contoured holder 116 remains in an upright position and capable of receiving the laryngoscope 14.

The contoured holder 116 is shaped to accommodate the laryngoscope 14 in the folded position as shown in FIG. 4.

In the preferred embodiment the arm 18 is made from stainless steel. The handle 16 and container 74 are made from Acrylonitrile butadiene styrene CABS). Although the handle 16 and container 74 of the preferred embodiment are formed from ABS, they need not be. For instance, the handle 16 and container 74 may be formed of any conventional material such as metal or plastic.

II. Additional Embodiments

A. Disposable Arm

Figure 16:
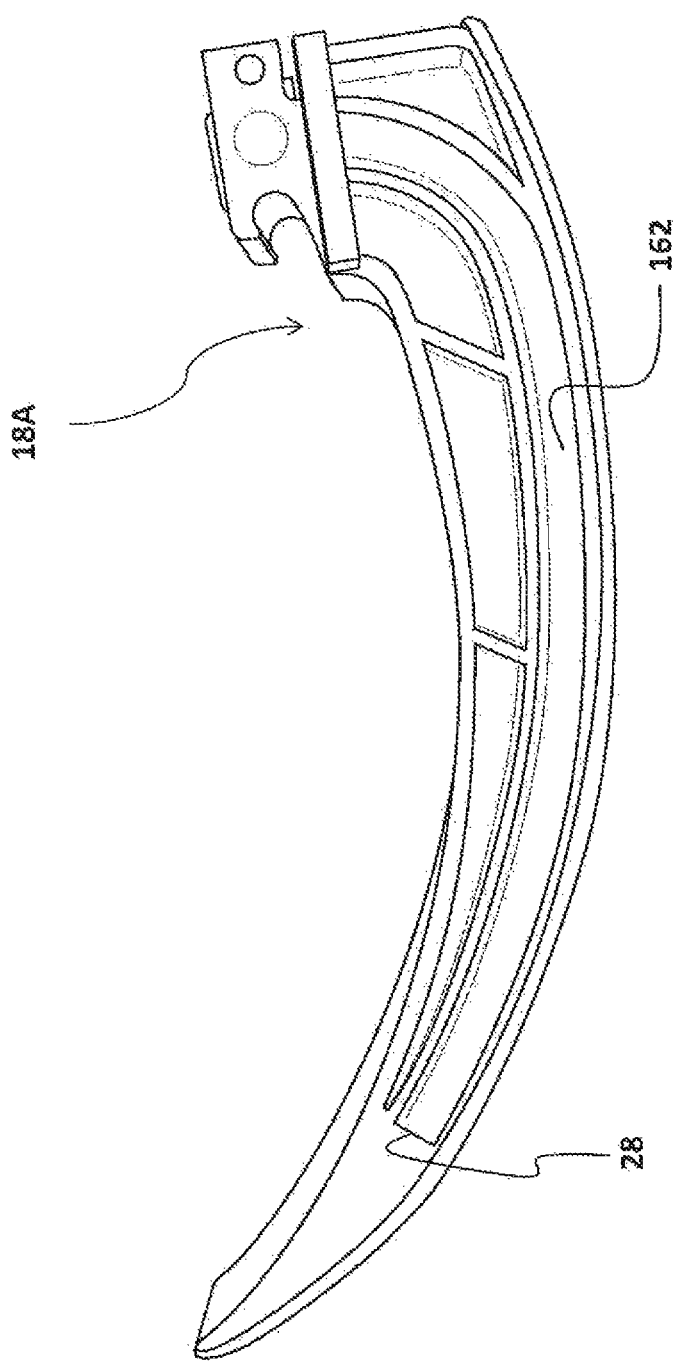
FIG. 16 is an isometric view of a disposable arm in accordance with a preferred embodiment.

Referring to FIGS. 16-22, in certain embodiments, the laryngoscope 14 comprises a handle 16 adapted to receive arms 18 of various configurations. In one embodiment, the handle 16 is adapted to receive a disposable arm 18A. As shown in FIG. 16, the disposable arm 18A is curved and may be removably coupled to the handle 16. In the preferred embodiment, this disposable arm 18A is formed from plastic and in some embodiments is at least partially clear so as to allow light emitted from a handle light element 160 to travel the length of the disposable arm 18A. For example, in a preferred embodiment, the handle light element 160 is a fixed LED housed within the handle 16. In this embodiment, the oral cavity is illuminated by using the clear disposable arm 18A as a light pipe that transmits the light from the handle light element 160 into the oral cavity.

In other embodiments, the disposable arm 18A is at least partially opaque such that light may be directed through certain parts of the disposable arm 18A and not others. For Example, a separate light pipe may be built into the disposable arm 18A. Referring to FIG. 16, in one such embodiment, the disposable arm 18A comprises a light tube 162 adapted to receive light emitted from the handle light element 160. Light received within the light tube 162 then passes through the transparent window 28.

Figures 18, 19:
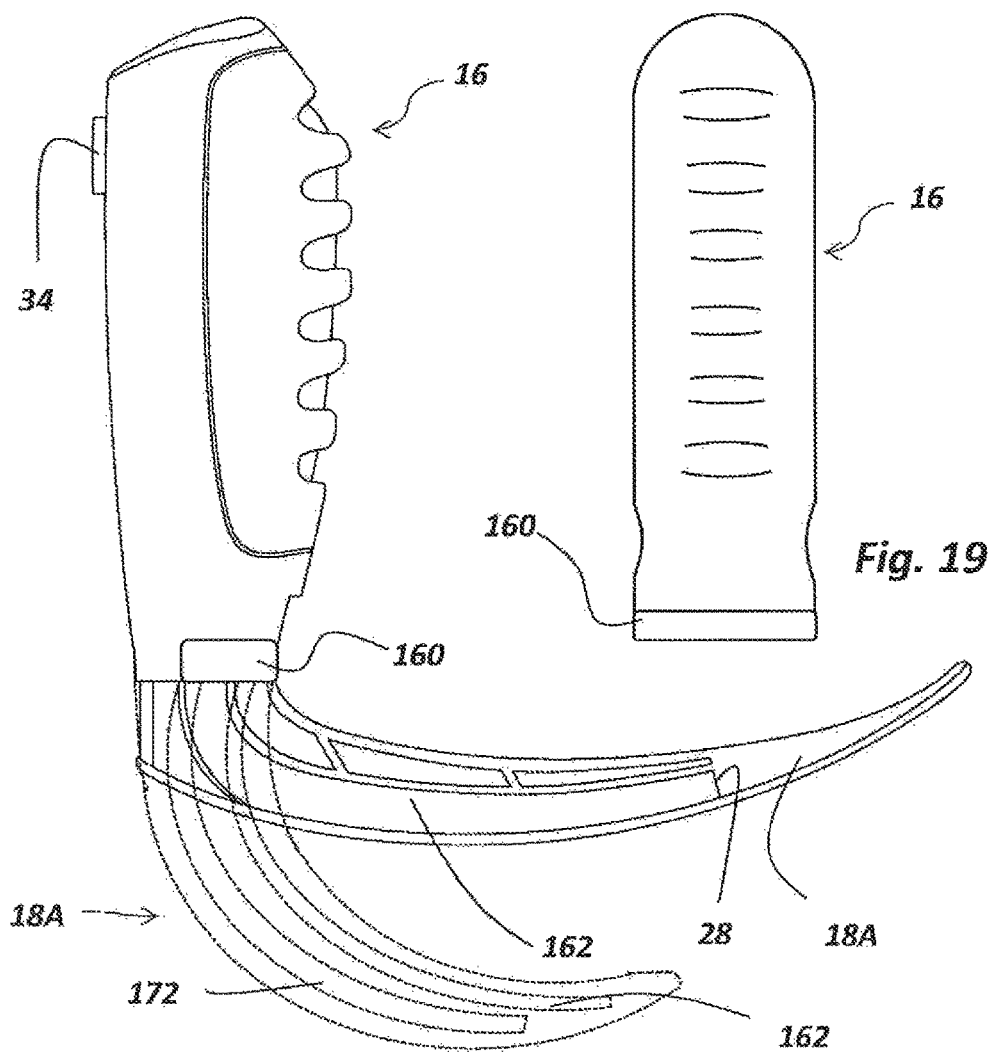
FIG. 18 is an elevation side view of the handle of FIG. 17 coupled to arms of different configurations.
FIG. 19 is a front elevation view of the handle in accordance with a preferred embodiment.

The disposable arm 18A may be of different configurations. Referring to FIG. 18, the disposable arm 18A can have an elongated and relatively flat configuration or a shorter more arcuate configuration. Thus, based upon clinician preference or patient needs, the user can choose a disposable arm 18A that is of a size and shape appropriate for the patient being administered to.

As will be discussed in more detail below, in one embodiment, the disposable arm 18A comprises a camera channel 172 adapted to receive a portion of an extendible camera assembly 170 comprising an extendible camera 22A. The camera channel 172 comprises a diameter slightly larger than the diameter of the portion of the extendible camera assembly 170 entering the camera channel 172. The camera channel 172 further comprises an open, or transparent end portion 176 to permit the extendible camera 22A to capture images.

Figure 20:
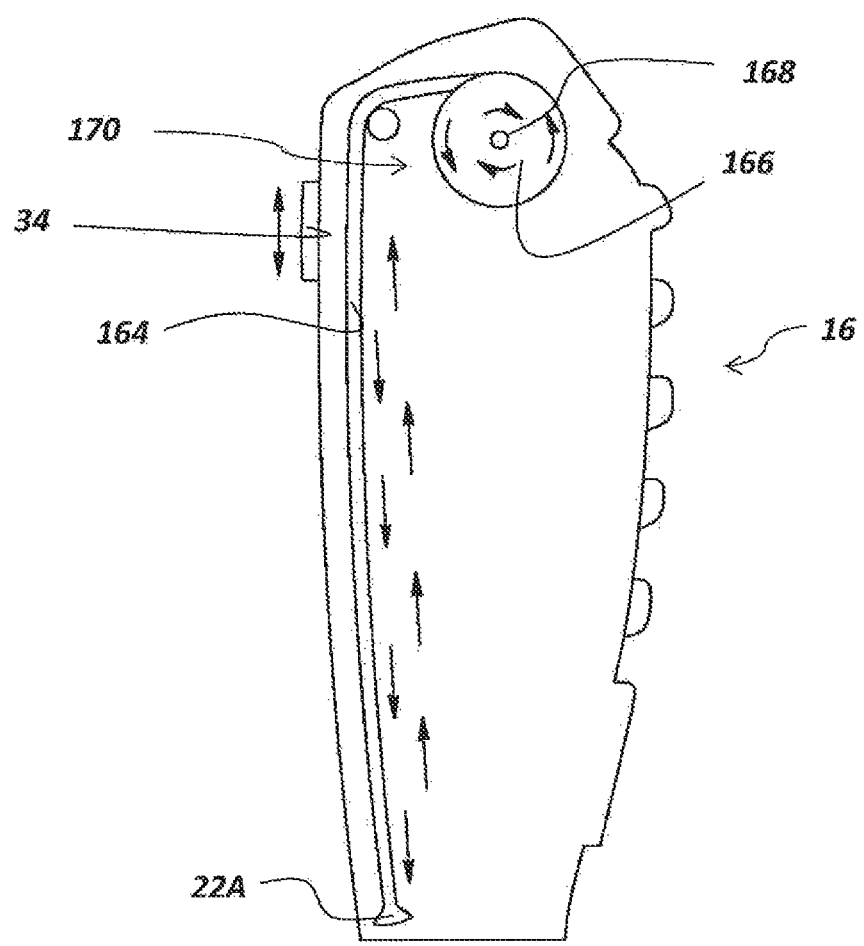
FIG. 20 is a cut-away side view of an inner portion of a handle of an alternative preferred embodiment.
Figure 21:
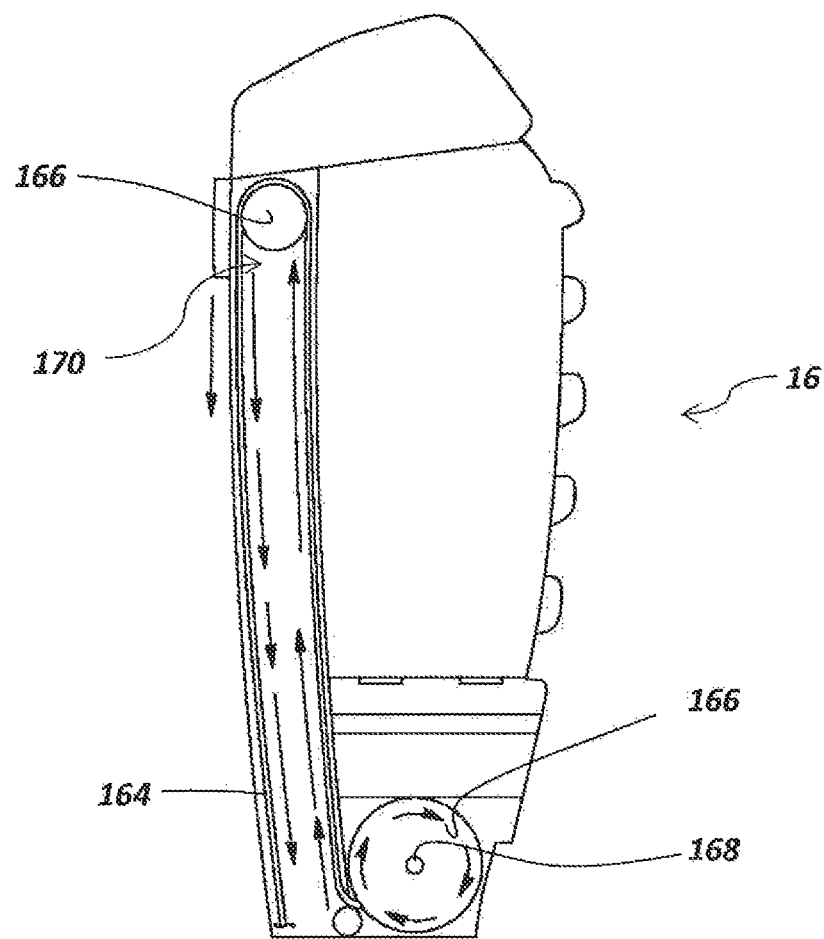
FIG. 21 is a cut-away side view of an inner portion of a handle of an alternative preferred embodiment.
Figure 22:
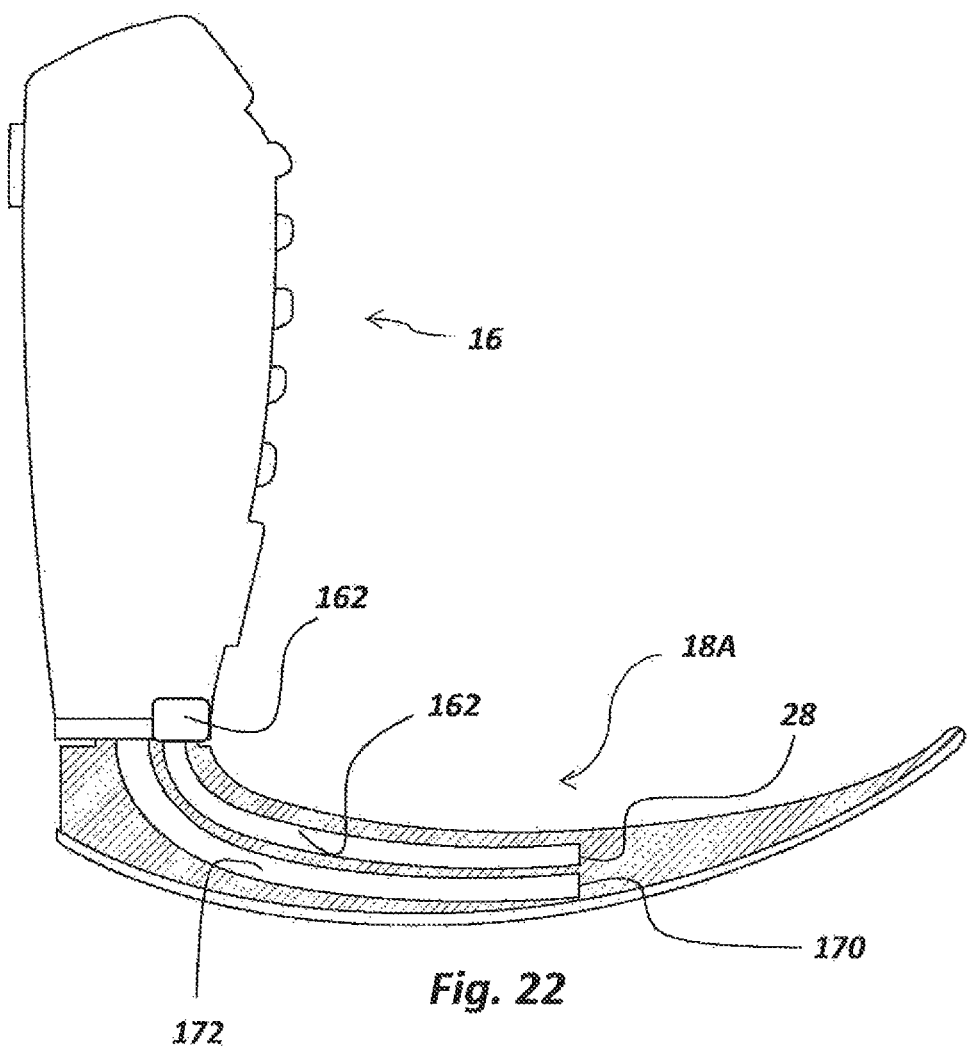
FIG. 22 is a cutaway view of the handle of FIG. 19 with an arm of an alternative embodiment.

The extendible camera assembly 170 is structured and arranged such that the extendible camera may be extended from a position within the handle 16 to a position outside the handle 16. Referring to FIGS. 20-22, in one aspect of the handle 16, the extendible camera assembly 170 further comprises a camera harness 164, and a spool 166. In some embodiments, the camera harness 164 is spoolably wrapped around a portion of the spool 166 positioned within the handle 16. A motor assembly 168 is adapted to selectively wind the spool 166 in a direction corresponding to retracting the extendible camera 22A and extending the extendible camera 22A, depending upon the selection of the user. Referring to FIGS. 20 & 21, the motor assembly 168 can be positioned in various positions within the handle 16. For example, the motor assembly 168 can be positioned at the top of the handle as shown in FIG. 20 or at the bottom of the handle, as shown in FIG. 21.

Although the handle 16 of a preferred embodiment comprises a motor assembly 168 comprising a DC motor, the extendible camera assembly 170 can be deployed using other mechanical means known in the art. Other types of motor assemblies 168 structured and arranged to permit the camera harness 164 to be extended and retracted may be used. For example, the camera harness 164 need not wrap around a spool 166. Rather, the motor assembly can be adapted with a drive shaft and gear that corresponds to the camera harness 164 configuration such that the camera harness 164 is moved linearly. Alternatively, the extendible camera assembly 170 can be deployed manually, for example, by turning the spool 166 or extension of the spool 166 by hand.

The camera harness 164 is sufficiently rigid to permit the camera harness 164 to be extended by pushing a portion of the camera harness 164. In some embodiments, the camera harness 164 comprises a toothed outside configuration which is cooperatively toothed to correspond to an outside configuration of the spool 166 or drive shaft gear. The camera harness 164 is communicatively coupled to the extendible camera 22A and the display unit 72 such that it is adapted to transmit images captured by the extendible camera 22A directly or indirectly to the display unit 72. In the preferred embodiment, the camera harness 164 is 2-3 mm wide.

In some embodiments, the extendible camera 22A automatically extends a predetermined distance upon attachment of the disposable arm 18A to the handle 16. For example, in some embodiments, the extendible camera 22A extends to a position proximate to an end of the camera channel 172. In some embodiments, the extendible camera 22A automatically retracts within the handle 16 upon detachment of the disposable arm 18A from the handle 16. In some embodiments the distance the extendible camera 22A extends is pre-set. In some embodiments, the distance the extendible camera 22A extends is variable depending upon the size and shape of the disposable arm 18A attached to the handle 16. In some embodiments, proximity or other sensors detect positions of certain portions of the extendible camera assembly 170 and regulate the distance the extendible camera 22A extends.

The extendible camera 22A is a CMOS camera comprising a 7 mm$^2$ head portion. However, other cameras 22 may be used including those incorporating charge-coupled device (CCD) technology and other sizes of head portions may be incorporated within the device. In some embodiments, the extendible camera 22A may include extendible camera light elements 174 such as LED's for illumination, for example, of the oral cavity. Alternatively, a fixed camera 22 may be housed within the laryngoscope handle 16. In this case, a fiber optic bundle, or other means of transmitting images, may be built into the disposable arm 18A.

In one or more of the embodiments discussed in this disclosure, the laryngoscope 14 is activated (powered on) by attaching the disposable arm 18A to the handle 16 and deactivated (powered off) by detaching or ejecting the disposable arm 18. Activating the laryngoscope by attaching the disposable arm 18A to the handle 16, in certain embodiments, sends a message to the display unit 72 instructing it to turn on. Similarly, detaching or ejecting the disposable arm 18A from the handle 16 produces a message sent to the display unit 72 instructing it to turn off.

In one aspect of the present invention, a user, using the thumb ejector switch 34, may eject the disposable arm 18A without physically touching the disposable arm 18A. As with other embodiments, the thumb ejector switch 34 may be positioned at the upper end of the handle 16 or at a lower end.

In some embodiment of the invention, the disposable arm 18A further comprises a bougie canal 26 running at least partially along the outside length that serves as a guide for the bougie 70. With the laryngoscope 14 properly placed, the practitioner may thread the bougie 70 through the disposable arm's 18A bougie canal 26 into the airway and use this bougie 70 as a guide for an ET tube (not shown). In the preferred embodiment, this canal 26 is open on one side 27 such that the bougie 70 may be inserted and removed through this open side 27. In the preferred embodiment, this canal with its open side 27 is "C" shaped. This "C" shape helps maintain the bougie 70 within the canal 26 while still allowing the bougie 70 to be removed through the open side 27. Although the canal 26 of the preferred embodiment is open and forms a "C" shape, the canal 26 need not be open and need not be "C" shaped. Rather, the canal 26 can be closed on the sides so as to completely surround the bougie 70 along its length and can be circular or any other suitable shape.

B. Additional Wireless Communication Embodiments

As referenced above and referring to FIG. 15, in certain aspects of the present invention, the laryngoscope 14 is adapted to wirelessly communicate with the display unit 72. In an alternative embodiment, wireless network communication between the laryngoscope 14 and the display unit 72 is established and secured via near field communication (NFC). In the preferred embodiment, operable portions of the display unit 72 and handle 16 must be brought to a distance of 4 cm or less (preferably to the point of touching) in order for communication to be established between the two 72, 16 (NFC activation). Alternatively, wireless communication may be established by pressing a button on the laryngoscope 14 and a button on the display unit 72 (manual activation).

Once activated manually or by NFC, the wireless communication is direct between the display unit 72 and laryngoscope 14 such that no external routers, amplifiers, switches or similar devices are used. A direct wireless communication between the display unit 72 and laryngoscope 14 helps prevent persons gaining unauthorized access to the communications between the display unit 72 and laryngoscope 14. For example, as the wireless network established between the display unit 72 and laryngoscope 14 is not through a hospital's Wi-Fi network, persons with access to the hospital's Wi-Fi network will not have access to the wireless network established between the display unit 72 and laryngoscope 14. In the preferred embodiment, the communication established between the display unit 72 and laryngoscope 14 is preferably through encrypted WI-FI or encrypted Bluetooth standards. However, the communication can be established through any suitable standard and/or protocol.

Once the wireless network communication is activated manually or by NFC, the laryngoscope images captured by the camera 22 or extendible camera 22A are processed by the CPU 152 and transmitted wirelessly to the display unit 72 receiver 142 such that the images are displayed on screen 88.

III. Matters Related to Disclosure as a Whole

While there has been illustrated and described what is, at present, considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed as the best mode contemplated for carrying out the invention, but that the invention will include all embodiments falling within the scope of this disclosure.

As used herein, the terms "a" or "an" shall mean one or more than one. The term "plurality" shall mean two or more than two. The term "another" defined as a second or more. The terms "including" and/or "having" are open ended (e.g., comprising). The term "or" as used herein is to be interpreted as inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

Reference throughout this document to "one embodiment," "certain embodiments," "an embodiment," or similar term means that, a particular feature, structure, or characteristic described in connection with the embodiment is included in at least one embodiment of the present disclosure. Thus, the appearances of such phrases in various places throughout this specification are not necessarily all referring to the same embodiment. Furthermore, the particular features, structures, or characteristics may be combined in any suitable manner on one or more embodiments without limitation. The detailed description illustrates by way of example, not by way of limitation, the principles of the invention. This description will clearly enable one skilled in the art to make and use the invention, and describes several embodiments, adaptations, variations, alternatives, and uses of the invention, including what is presently believed to be the best mode of carrying out the invention.

We claim:

1. A laryngoscope comprising a handle, the handle comprising, an interior portion, and an exterior portion;
    the handle further comprising a camera harness comprising a camera;
    the camera being moveable between first and second positions;
    the camera being retained within said interior portion when in the first position;
    the camera being exterior to the handle when in said second position; and
    at least a portion of the camera harness being retained within the handle when the camera is in said first and second positions.

2. The laryngoscope of claim 1, further comprising a motor adapted to move the camera between said first and second positions.

3. The laryngoscope of claim 1, further comprising an arm, said arm comprising a canal adapted to receive said camera when the camera is in the second position.

4. The laryngoscope of claim 1, the handle further comprising a light adapted to illuminate an area exterior to the handle.

5. The laryngoscope of claim 4, further comprising an arm, said arm comprising a light pipe adapted to accept illumination projected from the light and transmit such illumination beyond a distal end of said arm.

6. The laryngoscope of claim 5, said arm further comprising a canal adapted to receive said camera when the camera is in the second position.

7. The laryngoscope of claim 3, the camera moving from the first position to the second position upon coupling of the arm to the handle.

8. The laryngoscope of claim 7, the camera moving from the second position to the first position upon decoupling of the arm from the handle.

9. The laryngoscope of claim 8, the handle comprising an ejection element adapted to decouple the arm from the handle.

10. The laryngoscope of claim 3, the camera comprising a light source adapted to project light into an oral cavity.

11. A laryngoscope system, the system comprising a laryngoscope handle and a display unit:
    the handle and display unit each being adapted for wireless communication between the handle and the display unit;
    said wireless communication comprising first and second direct communication links between the handle and the display unit;
    said first direct communication link being through near field communication protocol; and
    said first direct communication link establishing and securing the second direct communication link.

12. The laryngoscope system of claim 11 further comprising an arm removably coupled to the handle.

13. The laryngoscope system of claim 12, the handle being adapted to power on upon coupling with the arm and to power off upon decoupling of the arm.

14. The laryngoscope system of claim 13, the display unit being adapted to power on upon coupling the handle with the arm and to power off upon decoupling of the arm from the handle.

15. An arm adapted to be removeably coupled to a laryngoscope handle, the arm comprising a canal adapted to receive a camera portion extending from the handle.

16. The arm of claim 15, the arm comprising a light pipe adapted to accept illumination projected from a light and transmit such illumination beyond a distal end of said arm.

17. The arm of claim 15, the arm further comprising a bougie canal adapted to receive a bougie.

18. The arm of claim 16, the arm being adapted for a single use such that the arm is disposable.

* * * * *